United States Patent
Teodorovic (10) Patent No.: US 10,222,634 B2
(45) Date of Patent: Mar. 5, 2019

(54) OPTICAL MEASUREMENT AID DEVICE

(71) Applicant: Optinno B.V., The Hague (NL)

(72) Inventor: Marko Teodorovic, The Hague (NL)

(73) Assignee: Optinno B.V., The Hague (NL)

( * ) Notice: Subject to any disclaimer, the term of this patent is extended or adjusted under 35 U.S.C. 154(b) by 0 days.

(21) Appl. No.: 15/643,572

(22) Filed: Jul. 7, 2017

(65) Prior Publication Data

US 2019/0011731 A1    Jan. 10, 2019

(51) Int. Cl.
  *G02C 13/00*    (2006.01)
  *H04N 7/18*    (2006.01)
  *G02C 7/02*    (2006.01)

(52) U.S. Cl.
  CPC .......... *G02C 13/003* (2013.01); *G02C 7/027* (2013.01); *G02C 13/005* (2013.01); *H04N 7/183* (2013.01)

(58) Field of Classification Search
  CPC .... G02C 13/005; G02C 13/003; G02C 7/027; A61B 3/111; A61B 3/0025
  USPC .................................................. 351/200–246
  See application file for complete search history.

(56) References Cited

U.S. PATENT DOCUMENTS

| | | | |
|---|---|---|---|
| 5,617,155 A * | 4/1997 | Ducarouge | A61B 3/11 351/200 |
| 5,640,219 A * | 6/1997 | Ramachandran | A61B 3/11 33/200 |
| 6,535,223 B1 | 3/2003 | Foley | |
| 7,296,357 B2 | 11/2007 | Katzman | |
| 7,384,144 B2 | 6/2008 | Ross-Messemer et al. | |
| 7,740,355 B2 * | 6/2010 | Sessner | G02C 13/005 351/204 |
| 7,896,493 B2 | 3/2011 | Welk et al. | |
| 8,231,220 B2 | 7/2012 | Baranton | |
| 8,459,792 B2 | 6/2013 | Wilson et al. | |
| 9,033,496 B2 | 5/2015 | Divo et al. | |
| 9,091,867 B1 | 7/2015 | Farache | |
| 9,198,576 B1 | 12/2015 | Barnes et al. | |
| 9,236,024 B2 | 1/2016 | Coon | |
| 9,323,075 B2 | 4/2016 | Silva et al. | |
| 9,759,934 B2 * | 9/2017 | Divo | G02C 13/005 |
| 2004/0189935 A1 | 9/2004 | Warden et al. | |
| 2010/0283844 A1 | 11/2010 | Sayag | |

(Continued)

FOREIGN PATENT DOCUMENTS

| | | |
|---|---|---|
| FR | 2766043 A1 | 1/1999 |
| FR | 2919395 A1 | 1/2009 |

OTHER PUBLICATIONS

Search report EP18181583.8.

*Primary Examiner* — Mohammed A Hasan
(74) *Attorney, Agent, or Firm* — N.V. Nederlandsch Octrooibureau; Catherine A. Shultz; Tamara C. Stegmann (57) ABSTRACT

A method of measuring parameters for eyeglasses includes a) providing a frame comprising a left eye rim, a right eye rim, and a bridge joining the left eye rim to the right eye rim; b) capturing a first image of a user wearing the frame, wherein the first image captures the left eye rim and the bridge of the frame on the user; c) capturing a second image of the user wearing the frame, wherein the second image captures the right eye rim and the bridge of the frame on the user; d) scaling the first image using a known measurement; e) determining one or more left lens parameters; f) scaling the second image using a known measurement; and g) determining one or more right lens parameters.

22 Claims, 7 Drawing Sheets

(56) References Cited

U.S. PATENT DOCUMENTS

| | | | |
|---|---|---|---|
| 2011/0242481 A1* | 10/2011 | Wada | G02C 13/005 351/204 |
| 2013/0125406 A1 | 5/2013 | Delort | |
| 2014/0240470 A1 | 8/2014 | Dias Da Silva et al. | |
| 2014/0240664 A1 | 8/2014 | Divo et al. | |
| 2016/0124249 A1 | 5/2016 | Haddadi et al. | |
| 2016/0171287 A1 | 6/2016 | Surkov et al. | |
| 2016/0299360 A1 | 10/2016 | Fonte et al. | |
| 2017/0168323 A1 | 6/2017 | Gardner | |

* cited by examiner

OPTICAL MEASUREMENT AID DEVICE

BACKGROUND

Typically when a person determines they need eyeglasses for vision correction, they go to an optician or optometrist who uses specialized equipment to determine the parameters required to ensure that the prescription and ophthalmic lenses are right for the person. Besides measuring the ophthalmic lens correction for the wearer, this typically includes measuring the pupillary distance, the fitting height or segment height, and possibly other parameters for individualized eyeglasses. This ensures that the frames and ophthalmic lenses are personalized and optimized for the wearer. Such specialized equipment, while producing very accurate measurements, is very costly, requires specialist training and knowledge, and typically takes up a lot of space within the optician's office. These measurements are used to either manufacture ophthalmic lenses (e.g., for prescription ophthalmic lenses such as progressives) and/or in properly centering and glazing ophthalmic lenses in frames (e.g., for stock ophthalmic lenses). Glazing is a term used to refer to the mounting or insertion of ophthalmic lenses in frames.

In recent years, companies have begun selling eyeglasses over the internet. There are typically two different systems for this. In a first system, described in U.S. Pat. No. 6,535,223, a person "virtually tries-on" eyeglasses by submitting a image of their face with a reference object on or near the face. The reference object is of a known size, and the image is scaled according to that. Virtual frames are placed over the image, and measurements such as pupillary distances can be calculated. However, such a system fails to take into account the differences in facial structure which cause frames to fit differently on different persons as well as the personal preference for where frames are worn on the nose (closer or further from the eyes). Thus, a virtual try-on method does not give accurate personalized measurements as to the person and the particular frame.

The second general method uses actual frames, and captures images and makes measurements, often using a known object for scaling, such as a coin or credit card held against the face in the captured image. One such system is shown in U.S. Pat. No. 9,091,867. This system allows a user to choose a frame, and then a calibrated frame which substantially matches the shape and size of the desired frame is provided. The user captures an image of the face with the frame on, and the calibration points on the frame are used to determine measurements for making the eyeglasses for the user, taking into account the preferred placement of the frame on the user. The ophthalmic lenses are glazed in the actual frame based on the measurements. However, these methods of measurement for online ordering are still not as accurate in capturing measurements as the methods typically used by opticians, and it can be costly to produce individual calibration frames for every frame design.

SUMMARY

According to a first aspect of the invention, a method of measuring parameters for eyeglasses includes a) providing a frame comprising a left eye rim, a right eye rim, a left temple, a right temple, and a bridge joining the left eye rim to the right eye rim; b) capturing a first image of a user wearing the frame, wherein the first image captures the left eye rim and the bridge of the frame on a user; c) capturing a second image of a user wearing the frame, wherein the second image captures the right eye rim and the bridge of the frame on a user; d) scaling and/or adjusting the first image using a known measurement; e) determining one or more left ophthalmic lens parameters; f) scaling and/or adjusting the second image using a known measurement; and g) determining one or more right ophthalmic lens parameters. Such a method can be used to determine very accurate ophthalmic lens parameters for manufacturing and/or glazing lenses into frames. By capturing each eye separately, each image can be separately scaled, adjusted and measured such that the most accurate measurements for the person can be determined.

According to an embodiment, the method further comprises aligning a capturing lens with the user's left eye prior to step b) and/or aligning a capturing lens with the right eye prior to step c). Optionally, the step of aligning a capturing lens with the left or right eye comprises placing the capturing lens directly in front of the left or right pupil at a set distance. Further optionally, the set distance is about 10 cm-30 cm. Proper alignment can ensure that the captured image is not skewed such that more accurate measurements can be taken. Placing the lens directly in front of the pupil can help to avoid parallax errors in measurement. A distance of 10 cm to 30 cm can ensure that the image is clear and sharp without the need for further image processing. Such a distance can also allow for a user to capture the image by him or herself without the need for another person to assist. Capturing images of one eye at a time, while the other eye is focusing on a distant object, reduces the possibility of eyes converging and the associated measurement error.

According to an embodiment, the known measurement is an eye iris. An eye iris has a standard size in adults of about 12 mm. Thus, the iris can easily be used as a known measurement in order to properly scale the image and convert measured image measurements into actual measurements for the ophthalmic lenses.

According to an embodiment, the one or more left ophthalmic lens parameters comprises one or more of a left side pupillary distance and fitting or segment height. The one or more right ophthalmic lens parameters can comprise one or more of: a right side pupillary distance and fitting or segment height. Such parameters can ensure lenses are personalized in manufacture and/or glazing for the user without having to see an optician and use their complicated equipment for accurate parameter measurements.

According to an embodiment, steps b) and/or c) further include aligning a capturing lens such that a set portion of the capturing lens aligns with an alignment feature on the frame. Optionally, the alignment feature could be a cross on the bridge, a circle, something printed on the frames or temporarily attached to the frames, and/or any number of alignment feature configurations.

According to an embodiment, the method further includes adjusting the first and/or second images for tilt. This can adjust for tilt around the capturing lens. Optionally, this can be done by having the first image also capture the right pupil, the second image also capture the left pupil, drawing a line through the right and left pupils of the captured image; and tilting the image such that the line is horizontal. This ensures an accurate measurement of parameters on the captured images.

According to an embodiment, the method further comprises capturing a first side image of a user wearing the frame; and determining a temple distance for the first side. Optionally, this can include scaling the first side image. Scaling can be done by attaching a feature, for example a sticker, with a known measurement to the frames such that the image can be scaled. The temple distance for the first side can then be measured from the scaled image. Alternatively, the frames could have a scaling or measurement feature directly on them, which could allow for scaling or simply reading a temple distance directly from the frame. A second side image can be captured and a second side temple distance could then also be determined in a similar manner. This can allow for the personalization of temples on frames, ensuring they are each adjusted by bending the tip of the temple so it fits behind user's ear and not, for example, according to an estimated temple distance or an exact same temple distance on each side if that is not appropriate for the user. This ensures that the frames feel secure and comfortable to individual users.

According to a further aspect of the invention, a system comprises a computer with a user interface; and a non-transitory computer readable program for causing the computer to perform the following steps when executed: instructing a user to capture and transmit a first image of the user with a frame on, with the first image showing the left eye and a bridge of the frame from a predetermined distance; instructing a user to capture and transmit a second image of the user with a frame on, with the second image showing the right eye and a bridge of the frame from a predetermined distance; receiving the first and second images from the user; scaling each of the first and second images based on the user's iris in each image; and determining a left pupillary distance using the scaled first image; and determining a right pupillary distance using the scaled second image. Such a system can allow for a user to be able to capture images which can be used for determining accurate parameters for manufacturing and/or glazing ophthalmic lenses in eyeglasses. This can allow a user to order eyeglasses with ophthalmic lenses manufactured and/or glazed optimally for their specific measurements, preferences and facial structure.

According to an embodiment, and further comprising the steps of: determining a left fitting height using the scaled first image; and determining a right fitting height using the scaled second image. The fitting height, sometimes known as segment height, is the distance between the centre of the pupil and a point directly below the pupil center of the eye where the opthalmic lens and rim connect or ophthalmic lens edge is located, in case of rimless frames. Determining a left and right fitting height can allow for the manufacture and/or glazing of ophthalmic lenses according to a user's exact measurements on each side, and is especially helpful for multifocal or high correction ophthalmic lenses.

According to an embodiment, and further comprising the steps of transmitting the left fitting height and the right fitting height to an ophthalmic lens ordering system and/or transmitting the left pupillary distance and the right pupillary distance to an ophthalmic lens ordering system. Determining accurate measurements for the fitting height and pupillary distance of each eye, and then transmitting to an ophthalmic lens ordering system allows for a system which can enable the ordering of eyeglasses optimized for the individual without requiring the individual to leave the home.

According to an embodiment, the system further comprises an image capturing device for capturing the first and second images and transmitting the first and second images. The image capturing device could be, for example, a simple camera found in nearly all smartphones or tablet computers.

BRIEF DESCRIPTION OF THE DRAWINGS

The present invention will be discussed in more detail below, with reference to the attached drawings, in which:

FIG. 4a shows a view of an image capture device capturing a side view of a user with frames on.

DESCRIPTION

Figure 1A:
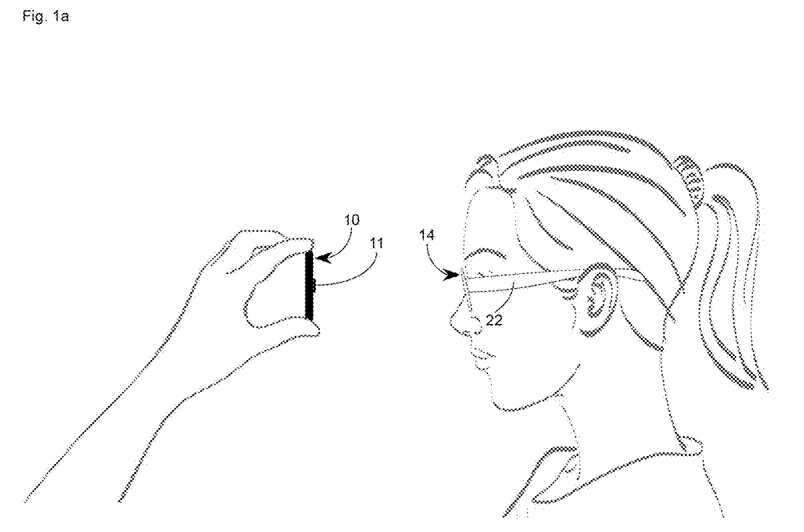
FIG. 1a shows a side view of a user and image capture device.
Figure 1B:
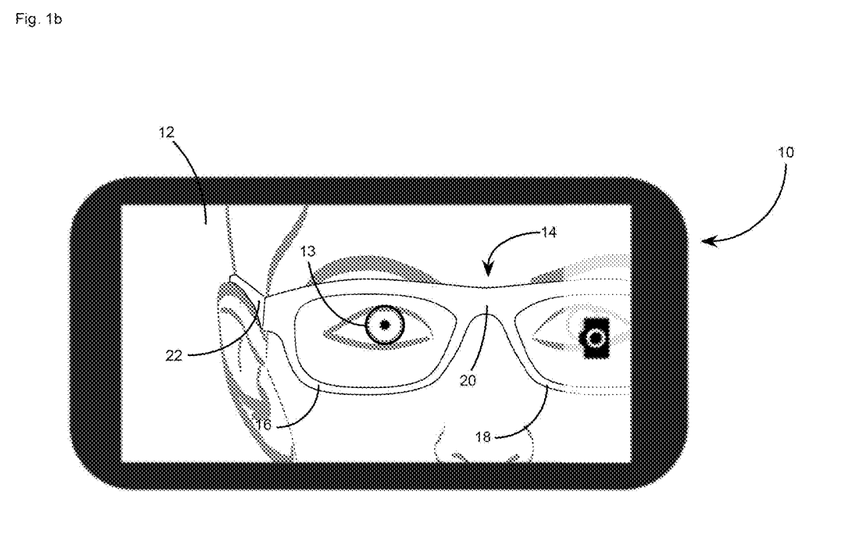
FIG. 1b shows a screen of the image capture device of FIG. 1a during alignment and capture of an image of a user's left eye.
Figure 1C:
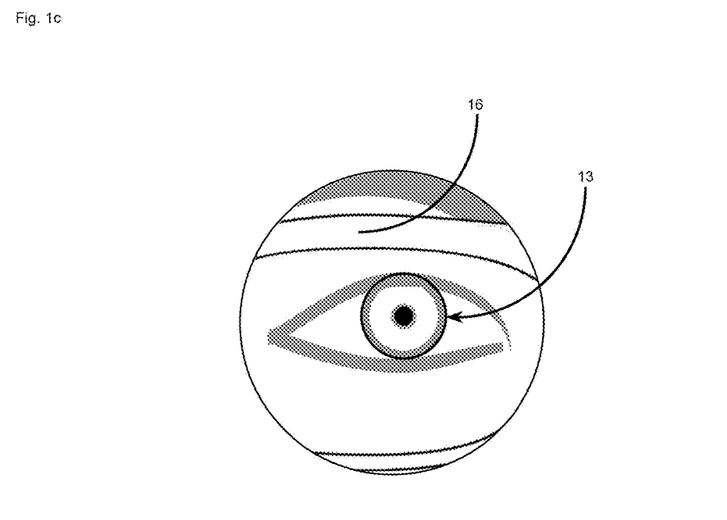
FIG. 1c shows a close-up portion of FIG. 1b.
Figure 1D:
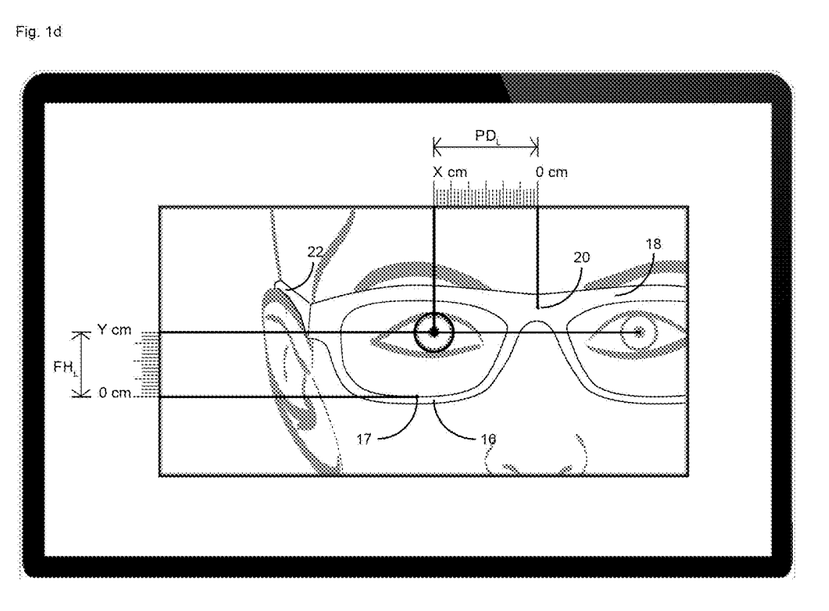
FIG. 1d shows the image captured from FIG. 1a with measurement distances plotted.
Figure 1E:
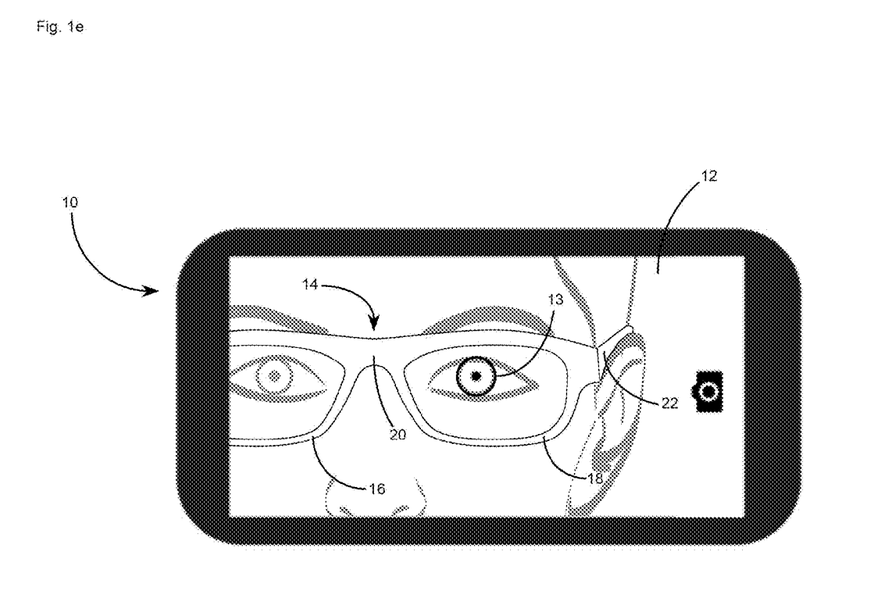
FIG. 1e shows the alignment and capture of an image of a user's right eye.
Figure 2:
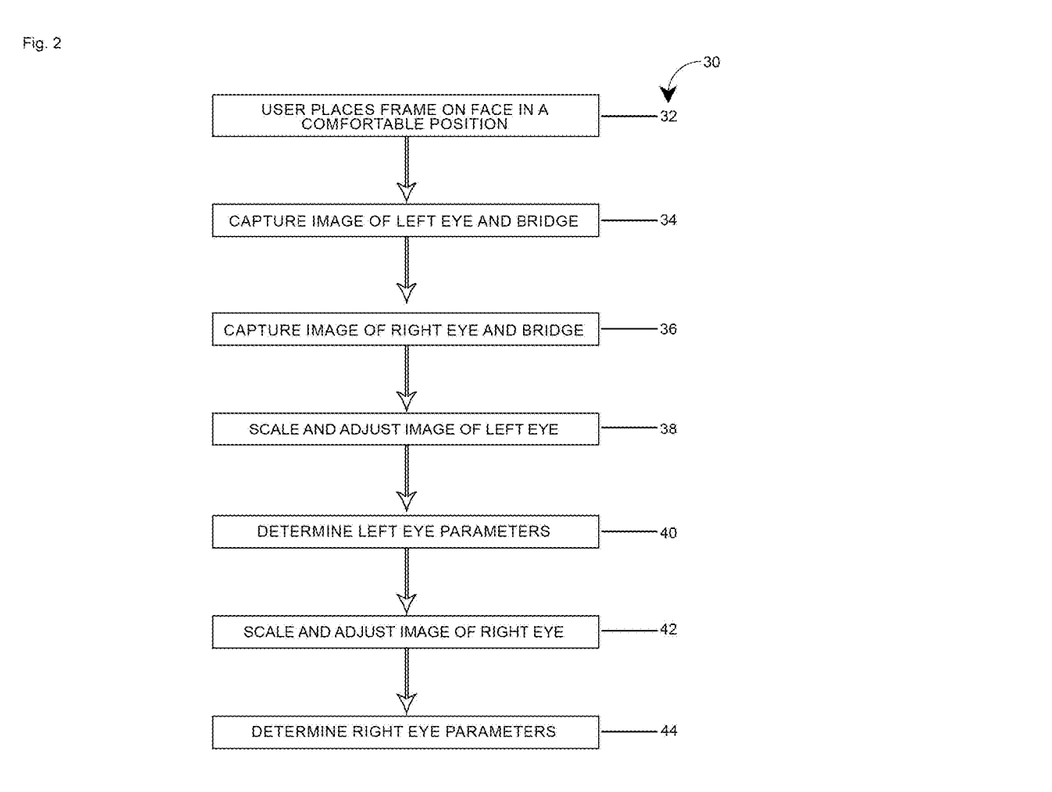
FIG. 2 shows a flow chart depicting a process of measuring a person for eyeglasses.

FIG. 1a shows a side view of a user and image capture device 10, FIG. 1b depicts a screen 12 of the image capture device 10 during alignment and capture of an image of a user's left eye, FIG. 1c shows a close-up view of a portion of FIG. 1b, and FIG. 1d shows the image captured from FIG. 1a, with measurement distances plotted, and FIG. 1e shows the alignment and capture of an image of a user's right eye. FIG. 2 shows a flow chart depicting a process of measuring a person for eyeglasses. The process with be discussed in combination with the images of the process shown in FIGS. 1a-1e.

FIGS. 1a-1e include image capturing device 10 with capturing lens 11, screen 12 and alignment feature 13; frame 14 with left eye rim 16, right eye rim 18, bridge 20 and temples 22; left pupillary distance PDL and left fitting height FHL. Method 30 of measuring for eyeglasses includes steps 32-44, which will be discussed in relation to FIGS. 1a-1e.

Image capturing device 10 is a handheld electronic device, and could be, for example, a smart phone, a tablet computer or other handheld device which is capable of capturing an image and has a display. The image capturing device 10 can include a computer system, software, an application and/or other configuration to perform at least parts of method 30.

Frame 10 is an actual frame with a temporary non-corrective lens which is selected by a user, for example from pictures on an internet website, and sent to the user. As shown in step 32 of method 30 and FIG. 1a, the user places the frame 14 on his or her face in a comfortable position where the user intends to wear frame 14. In some embodiments, the user may enter information regarding the specific frame into the image capturing device 10 or a related application to identify the frame 14 used for method 30, and/or a customer number or other input associated with the user to identify the user to the system. This could be in the form of, for example, a QR code, a barcode on the shipping parcel, a picture of the frame, a related number or other method for identifying and storing information regarding frame 14. This reference could be used in other steps as well as initially or instead of initially, for example, entering user and/or frame identifying information just before sending measurements and/or images.

To prepare for the image capture, the user looks at a point in the distance straight in front of the eyes (approximately at the same height as the eyes) with the frame 14 on the face, for example, a point 3-4 meters away to allow the eyes to be in a natural position without significant convergence for viewing an object through the frame 14. This ensures that the user's eyes are positioned correctly for making pupillary distance and fitting height measurements. Next, as depicted in step 34 and FIGS. 1*a*-1*c*, an image capture device 10 is used to capture a first image, showing the left eye, the bridge 20 of frame 14, and pupil of the right eye to the side of the image. Image capture device 10 can use alignment feature 13 to ensure that the capture device 10 is properly aligned and positioned relative to the user for capturing an image directly in front of the user's left eye. In this example, alignment feature 13 is circle with a central dot. The image capture device 10 is moved such that the circle aligns to frame the iris of the user (see FIG. 1*c*) and the central dot is in the middle of the pupil, thereby ensuring the captured image is properly aligned and that the capture device 10 is positioned at an appropriate distance. This distance is usually about 15 cm-30 cm, though could be in the range of 10 cm-50 cm, or another range depending on the optical or digital zoom features of the device 10. Further alignment features, for example, relating to tilt and/or direct alignment of the lens 11 with the eye could be used (see, for example, FIG. 3).

After alignment with alignment feature 13, an image is captured by pressing a capture button or screen icon on capture device 10. In some embodiments, the image could be automatically captured when the alignment features are aligned with the iris. This could help in the capturing of images without the need for a second person to assist the user. The same procedure is used for aligning with and capturing the user's right eye, bridge 20 and pupil of the left eye to the side of the image, as depicted in FIG. 1*e* and step 36 of method 30.

Captured images then need to be scaled using a known measurement (steps 38 and 42). The iris has a standard size across most adults, and is used as the known measurement from which to scale the captured image. Assuming a standard iris diameter of 12 mm, the measurements from the image can be scaled accordingly so that each image can be used to determine parameters for manufacturing and glazing the lenses for frame 14. The scaling can be done, for example, by zooming in or out on the captured image such that the iris is a known size, for example such that the iris in the image fits into a known size circle.

Additionally, the image can be adjusted by drawing a line through the center of both pupils, and rotating the image so that this line is horizontal to ensure there is no tilt in the image around the axis of the camera lens 11 and horizontal lines of the screen (see FIG. 1*d*). As tilt can lead to significant error in the measurements, this ensures more accurate measurement. As shown in FIG. 1*d*, a left pupillary distance PDL can be determined from the first scaled image by measuring a distance from the center of the left pupil to the center of the bridge 20 of frame 14 to come up with the actual left pupillary distance for glazing the lens.

The pupillary distance PDR of the right eye is determined in the same manner, scaling the image and adjusting for tilt, and then using the scaled image of the right eye and bridge 20 to determine the right pupillary distance. The center of bridge can be estimated, measured from known frame parameters, or it could be marked on the frame, for example with a temporary marker such as a sticker.

When any ophthalmic, and especially multifocal, lenses are desired, the left fitting height FHL can be determined by measuring the image from point 17 at the bottom of the lens directly below the pupil to the center of the pupil on the scaled image (FIG. 1*d*). The right fitting height is determined in the same manner, using the scaled image of the right eye and measuring from a bottom of the lens directly below the pupil to a center of the pupil.

The steps 32-44 of method 30 can be done in the capturing device 10, for example, as part of an application, and/or using a computer with a user interface and software to instruct the user, a processor and/or other device 10 components for carrying out the method. Optionally, only some of the steps, such as steps 32-36 could be facilitated through prompts on the capturing device 10 or another device. Thereafter, capturing device 10 could send the images captured in steps 34 and 36 elsewhere for scaling and/or adjusting images and determining parameters. This could be, for example, through email, submission through a website or sent via an application, and a computer system would receive the images. The scaling of images, adjusting for tilt and determining parameters could be done through software, and/or could be at least partially done manually with the scaled pictures on the computer system receiving the captured images. For example, if at least partially performed manually, a technician could identify the middle of bridge 20 and point 17 at the bottom of right or left eye ophthalmic lens, and the center of the pupils in the captured images, and then measurements could be taken for the pupillary distance and fitting height based on the identified points by the technician. The steps 38-44 of scaling the images and determining eye parameters can be done in a different order than shown.

After the pupillary distances and fitting heights have been determined, these measurements can be sent to an ophthalmic lens ordering system, which can instruct how to manufacture ophthalmic lenses for frame 14 according to the parameters.

By capturing images of each eye separately, and using each separate image to determine lens parameters according to each eye, more personalized ophthalmic lenses can be ordered and/or produced for the user. By capturing each eye separately, and then determining a right pupillary distance and a left pupillary distance, each side may be determined for a specific user. When one image is captured and used to determine pupillary distance, this measurement is often inaccurate for two major reasons: converging of the eyes and asymmetric faces. The eyes tend to converge to look at the lens capturing the image in front of the person when one image is taken of both eyes, especially when image capture device is closer to the person. This convergence of the eyes results in a measured pupillary distance which is less than the actual pupillary distance for the person when they are looking at a distant object. The actual pupillary distance is needed as a parameter for correctly manufacturing and glazing the ophthalmic lenses. By having the user look into the distance and maintain the gaze while each individual eye image is captured, the current method and system is able to measure a more accurate pupillary distance that is not affected by convergence. A user looks at an object or point in the distance, and one eye maintains that gaze while the capturing lens is placed in the path of the eye being captured so that the object or point in the distance and the capturing lens overlap. In this manner, the image can be captured of each eye for pupillary distance measurements that are not affected by convergence.

Secondly, user's faces are often not exactly symmetric. By calculating a left pupillary distance to the center of bridge 20 and a right pupillary distance to the center of bridge 20, more accurate pupillary distances can be determined for the user, resulting in eyeglasses which are made according to each eye of the user. Fitting height is similarly measured accurately as to each eye, therefore allowing for the production of eyeglasses which are ideal for the specific user, and not based on an assumption of facial symmetry. By using the method 30 and system shown, accurate lens parameters can be determined remotely without having to go to an optician. This allows for making comfortable eyeglasses with accurate personal parameters without requiring the individual to leave his or her home.

By using a real frame 14 for fitting and image capturing, the user will have a better feel for how they prefer the specific frame 14 and eyeglasses to sit on the face. This can result in more comfortable eyeglasses and more accurate measurements in determining parameters for personalized ophthalmic lenses and eyeglasses.

Figure 3:
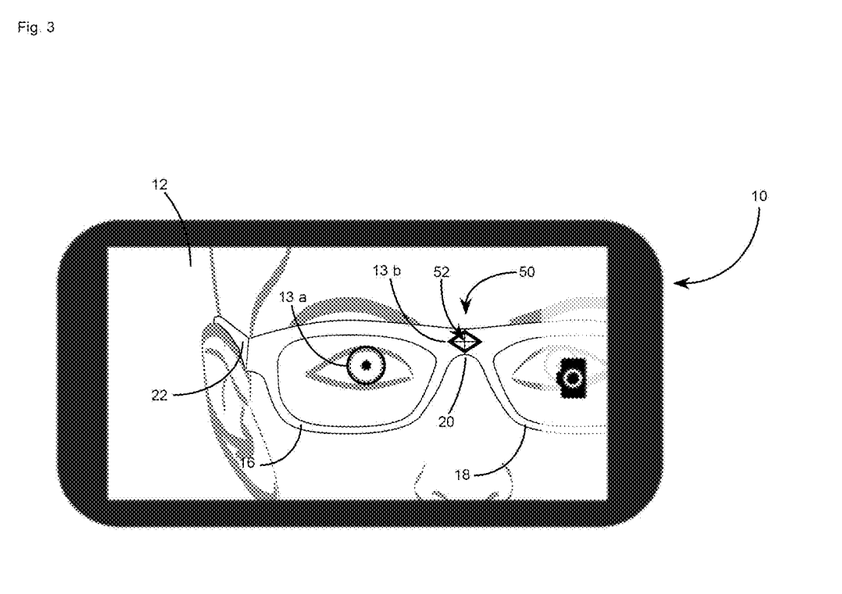
FIG. 3 shows the alignment and capture of an image of a user's left eye using a mock frame with a central reference marking.

FIG. 3 shows a further embodiment of the system, showing the alignment and capture of an image of a user's left eye using a mock frame 50 with a central reference marking 52. Similar reference signs are used for similar parts as in FIGS. 1a-2. FIG. 3 shows frame 50 with alignment feature 52, left eye rim 16, right eye rim 18, bridge 20 and temple 22; and capturing device 10 with screen 12 and alignment features 13a, 13b.

FIG. 3 works in a similar manner to the system shown in FIGS. 1a-2, only in this embodiment, a mock-up frame is made and used. This is formed in the shape of a selected real frame, and can be, for example, light-weight plastic or another printed medium. Frame 50 includes alignment feature 52 in the form of a cross at the center of bridge 20, though other alignment features in place of or in addition to could be used with frame 50. Such features could be a ruler printed directly onto the frames and/or other markings.

When capturing an image, alignment features 13a and 13b on screen 12 are used to align capture device 10 with the user and frame 50. Alignment feature 13a, in this embodiment dot and circle, is aligned with iris and pupil to ensure the capture device 10 is correctly positioned and at a proper distance from the user for capturing the image. Image capture device 10 is positioned such that alignment feature 13b fits around alignment feature 52. This can ensure capture device 10 is properly aligned with the user and is not tilted or skewed for capturing an image. Such proper alignment at two different points can ensure the image is not distorted and accurate parameters are determined from the images captured. In addition, the use of mock-up frames 50 can allow for one or more alignment features to be printed directly onto frames 50 for easier alignment at the stage of capturing of the images, as well as assist in easier determination of parameters by providing more scaling features. The use of mock-up frames can also enable easier shipping, removing the chances of damaging the actual desired frames during the shipping and/or measuring process.

Such a method and system allows for accurate determination of pupillary distance and fitting height for ophthalmic lens production and/or glazing with a small and simple process a user is able to perform at home, without complicated or expensive equipment. A standard camera included in most smart phones would be sufficient to perform the image capturing, and the user simply has to capture images of each eye while wearing a specific frame in a comfortable position. The captured images, which include one eye, the bridge and the pupil of the other eye, can be scaled and/or adjusted using the iris, and accurate parameters for manufacturing and/or glazing the ophthalmic lenses in the frame can be determined. The capturing of each eye separately allows for determining more accurate lens parameters to avoid distortions from convergence and asymmetric faces. The use of actual (as opposed to virtual) frames allows a person to decide where the frames feel most comfortable on them, for more accurate pupillary distances and fitting height measurements. By providing a simple way of determining fitting height accurately, eyeglasses with multi-focal or any single vision (monofocal) ophthalmic lenses may be ordered from the comfort of a user's home.

Figure 4A:
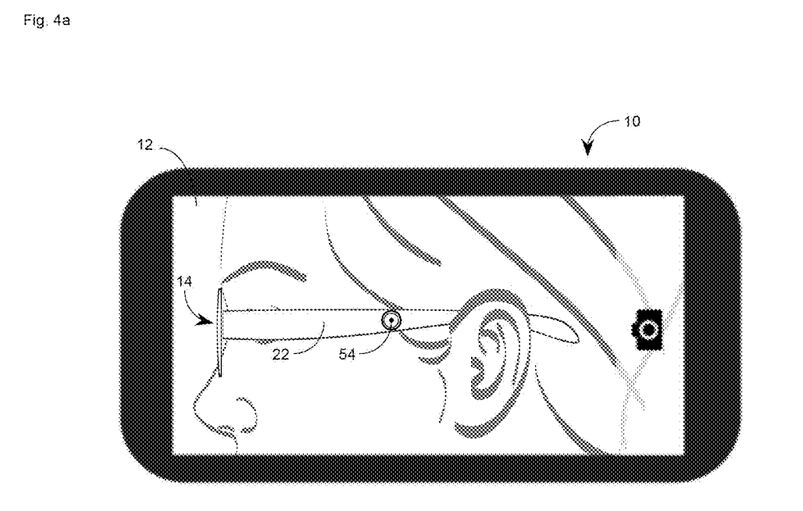
Figure 4B:
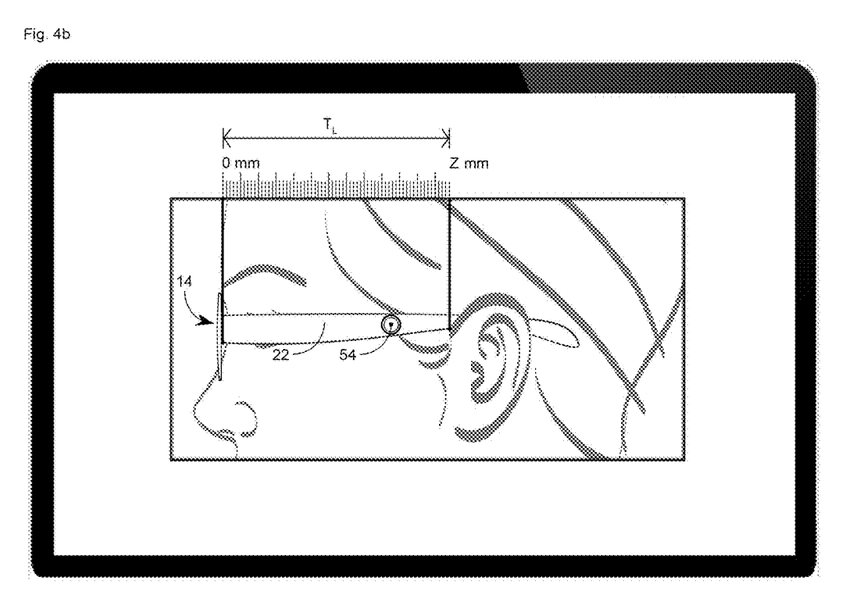
FIG. 4b shows an image captured from FIG. 4a with measurement distances shown.

FIGS. 4a-4b show a user capturing a side view wearing frames 14 to determine temple measurements. FIG. 4a shows an image capturing device 10 with a screen 12 capturing a right side view of a user wearing frames 14 with temple 22 and temple scaling feature 54. FIG. 4b shows a measurement of the left temple distance TL. Temple scaling feature 54 can be something with a known measurement, for example a sticker that can be temporarily connected to frames and visible to allow for scaling of the image shown in FIG. 4b. The scaled image can then be used to determine the left temple distance TL by measuring the distance from the temple end at the hinge 22 to the position of a user's ear, as shown in FIG. 4b.

This could be done as part of method 30, for example, capturing images of the left and right temples 22, respectively, after or before the capturing of images shown in steps 34-36. The scaling can be performed using a known measurement of the temple scaling feature 54, and then left and right temple distances can be determined after aligning the photograph so that the temple is horizontal on the screen, similar to the scaling and determining of eye parameters in steps 38-44 of method 30.

The left and right temple distances can then be used for knowing exactly where to bend each temple 22 to optimally fit an individual user. These temple measurements could be used by an optician who is glazing the frame to adjust the temples to the needs of the individual user for better fit and comfort.

Figure 5:
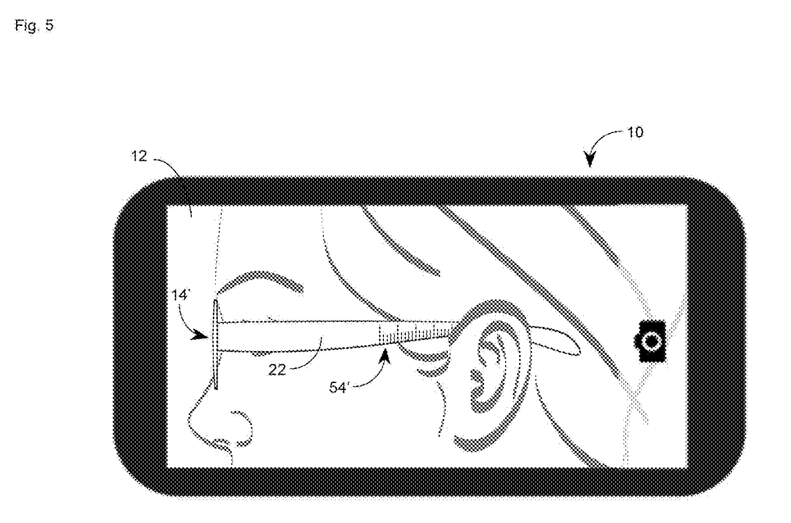
FIG. 5 shows a view of an image capture device capturing a side view of a user wearing measurement frames.

FIG. 5 shows a view of an image capture device capturing a side view of a user wearing measurement frames 14'. The measurement frames can be plastic frames which are formed to be similar to those a user is interested in buying. The measurement frames can have a scaling feature 54' directly printed or formed on the frame 14' such that no feature needs added for the image capturing and scaling. The other steps for determining the temple measurements are the same. In some embodiments, the scaling feature 54' on measurement frames is a ruler starting at the hinge of the temple, such that a measurement of the distance for each of the left and right temple distances can be directly read from the ruler without even having to scale the images.

Such a method and system which allows for accurate measurements of each of the left and right temple distances can further personalize frames to ensure that the frames fit the user in a comfortable and secure manner. Scaling features 54, 54' allow for scaling the captured image and/or accurately determining a measurement of where the temple 22 should be bent on each side for a specific user. As with other eye parameters, people often do not have exactly symmetric left and right ear positions. Thus, capturing images to determine left and right temple distances separately can result in glasses that feel secure and comfortable on a user. As with the other steps of method 30, a user can capture the images from their own home, allowing for the ordering of very personalized frames 14 without needing to visit a specialist.

The computer system(s), embodied in device 10 and for analysis, used for the system and methods described may represent a generic platform that may include components that may be in a server or another computer system. The computer system(s) may execute, by a processor or other hardware processing circuit, the methods, functions and other processes described herein. These methods, functions and other processes may be embodied as machine readable instructions stored on computer readable medium, which may be non-transitory, such as, for example, hardware storage devices. The computer system(s) that may implement or execute machine readable instructions performing some or all of the methods, functions and other processes described herein. The computer system may include a network interface for connecting to a network. Other known electronic components may be added or substituted in the computer system.

While the methods have been described in relation to a number of steps, some executed manually, many of these steps could be performed automatically. For example, the capturing, scaling, adjusting for tilt and/or sending of images or other information could be automatically performed by the system.

The communication and data transfer between image capturing device 10 and other systems for scaling and/or determining parameters may be through a network connection, or through a wireless connection.

While the description has referred to a user, this can be one or more persons associated with the system or method, including a user wearing the frames, another user which could be capturing the image and/or a further user which could be using the method in association with a computer program or application. While the description has referred to eyeglasses, other terms can be used, including spectacles, glasses, etc. The term ophthalmic lenses has generally been used to refer to the corrective lenses held by the frame, though they can be referred to as simply lenses or through other terms.

The description has referred to left or right pupillary distance, which is sometimes called half or mono pupillary distance and refers to the distance from the center of the left or pupil to the center of the bridge of frames, as depicted in FIG. 1d.

While the description and figures have shown frames with rims, the method and system can be used for rimless frames as well, with the fitting height measured from the bottom of the lens (instead of the point where the lens meets the eye rim).

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular or preferred embodiments disclosed, but that the invention will include all embodiments falling within the scope of the appended claims.

The invention claimed is:

1. A method of measuring parameters for eyeglasses, the method comprising:
   a) providing a frame comprising a left eye rim, a right eye rim, a bridge joining the left eye rim to the right eye rim and temples;
   b) capturing a first image of a user wearing the frame, wherein the first image captures the left eye rim and the bridge of the frame on the user;
   c) capturing a second image of the user wearing the frame, wherein the second image captures the right eye rim and the bridge of the frame on the user;
   d) scaling the first image using a known measurement;
   e) determining one or more left ophthalmic lens parameters comprising left side pupillary distance;
   f) scaling the second image using a known measurement; and
   g) determining one or more right ophthalmic lens parameters comprising right side pupillary distance.

2. The method of claim 1, and further comprising aligning a capturing lens with the user's left eye prior to step b).

3. The method of claim 2, wherein the step of aligning a capturing lens with the user's left eye comprises placing the capturing lens directly in front of the left pupil at a set distance.

4. The method of claim 3, wherein the set distance is about 10 cm-30 cm.

5. The method of claim 1, and further comprising aligning a capturing lens with the user's right eye prior to step c).

6. The method of claim 5, wherein the step of aligning a capturing lens with the user's right eye comprises placing the capturing lens directly in front of the right pupil at a set distance.

7. The method of claim 6, wherein the set distance is about 10 cm-30 cm.

8. The method of claim 1, wherein the known measurement is an eye iris.

9. The method of claim 1, wherein the one or more left lens parameters further comprises fitting height.

10. The method of claim 1, wherein the one or more right lens parameters further comprises fitting height.

11. The method of claim 1, wherein steps b) and/or c) further include aligning a capturing lens such that a set portion of the capturing lens aligns with an alignment feature on the frame.

12. The method of claim 1, and further comprising adjusting the first and/or second images for tilt.

13. The method of claim 12, wherein the first image also captures the right pupil, the second image also captures the left pupil, and the step of adjusting the first and/or second images for tilt comprises:
   drawing a line through the centers of the right and left pupils of the captured image; and
   tilting the image such that the line is horizontal.

14. The method of claim 1, and further comprising
   capturing a first side image of a user wearing the frame; and
   determining a temple distance for the first side.

15. The method of claim 14, and further comprising scaling the first side image.

16. The method of claim 1, wherein step d) and/or step f) comprise scaling using a marker strip connected to and/or a part of the frames.

17. A system comprising:
   a computer with a user interface; and
   a non-transitory computer readable program for causing the computer to perform the following steps when executed:

instructing a user to capture and transmit a first image of the user with a frame on, with the first image showing the left eye and a bridge of the frame from a predetermined distance;

instructing a user to capture and transmit a second image of the user with a frame on, with the first image showing the right eye and a bridge of the frame from a predetermined distance;

receiving the first and second images from the user;

scaling each of the first and second images based on the user's iris in each image; and determining a left pupillary distance using the scaled first image and the distance between the center of the pupil and a center of the bridge on the first image; and determining a right pupillary distance using the scaled second image and the distance between the center of the pupil and a center of the bridge on the second image.

18. The system of claim 17, and further comprising the steps of:

determining a left fitting height using the scaled first image and the distance between the center of the pupil and a lowest point of a left eye lens directly below the pupil center on the first image; and determining a right fitting height using the scaled second image and the distance between the center of the pupil and a lowest point of a right eye lens directly below the pupil center on the second image.

19. The system of claim 18, and further comprising the steps of:

transmitting the left fitting height and the right fitting height to an ophthalmic lens ordering system.

20. The system of claim 17, and further comprising:

an image capturing device for capturing the first and second images and transmitting the first and second images.

21. The system of claim 17, and further comprising the steps of:

transmitting the left pupillary distance and the right pupillary distance to an ophthalmic lens ordering system.

22. The system of claim 17, and further comprising the steps of:

determining a left temple distance using a captured left side image; and determining a right temple distance using a captured right side image.

* * * * *